United States Patent [19]

Kompis

[11] Patent Number: 4,599,416

[45] Date of Patent: Jul. 8, 1986

[54] PROCESS FOR THE PREPARATION OF AQUEOUS SOLUTIONS OF POTENTIATED SULFONAMIDES

[75] Inventor: Ivan Kompis, Oberwil, Switzerland

[73] Assignee: Hoffmann-La Roche Inc., Nutley, N.J.

[21] Appl. No.: 414,694

[22] Filed: Sep. 3, 1982

[30] Foreign Application Priority Data

Sep. 23, 1981 [CH] Switzerland .......................... 6140/81

[51] Int. Cl.$^4$ ........................................... C07D 403/12
[52] U.S. Cl. ..................... 544/296; 544/224; 544/295; 544/297; 544/324; 544/325; 544/336
[58] Field of Search ............... 544/224, 324, 325, 336, 544/297, 295, 296

[56] References Cited

PUBLICATIONS

McElvain, *The Characterization of Organic Compounds*, Rev. Ed., 1960, The MacMillan Co., N.Y., pp. 59–63, 147.

*Primary Examiner*—Glennon H. Hollrah
*Assistant Examiner*—James H. Turnipseed
*Attorney, Agent, or Firm*—Jon S. Saxe; Bernard S. Leon; William G. Isgro

[57] ABSTRACT

Aqueous solutions of antibacterially active sulfonamides and sulfonamide potentiators, which are suitable for parenteral administration and which contain no organic solvent, are prepared by reacting a sulfonamide RH with an aldehyde R$^1$CHO to give a compound of the formula R$^1$CH(R)$_2$ and dissolving said compound in water together with the sulfonamide potentiator.

12 Claims, No Drawings

PROCESS FOR THE PREPARATION OF AQUEOUS SOLUTIONS OF POTENTIATED SULFONAMIDES

BRIEF SUMMARY OF THE INVENTION

Aqueous solutions of antibacterially active sulfonamides and sulfonamide potentiators, which are suitable for parenteral administration and which contain no organic solvent, are prepared by reacting a sulfonamide RH with an aldehyde $R^1CHO$ to give a compound of the formula $R^1CH(R)_2$ and dissolving said compound in water together with the sulfonamide potentiator.

DETAILED DESCRIPTION OF THE INVENTION

The invention is concerned with a process for the preparation of aqueous solutions of potentiated sulfonamides.

Combinations of sulfonamides and sulfonamide potentiators, the latter being referred to hereinafter as potentiators for the sake of simplicity, are used extensively for the treatment of bacterial infections in human and veterinary medicine. Because of the different solubility characteristics of the sulfonamides and of the potentiators and because a weak base (potentiator) must be combined with a weak acid (sulfonamide) in non-stoichiometric amounts, the manufacture of pharmaceutically usable solutions, for example, injection solutions, of combinations of these substances causes difficulties. The hitherto proposed solutions have not been entirely satisfactory when considered in connection with the compatibility of the solvent, especially large amounts of organic solvent; the liberation of the active substances or the stability of the preparations, or also in connection with the costs of preparing the solutions. An object of the invention is to remedy these deficiencies by providing pharmaceutical preparations in aqueous form or preparations convertible in a simple manner into an aqueous form, which possess satisfactory compatibility and activity, have a high active substance concentration and physiologically favorable pH-value, are sufficiently stable and contain no expensive adjuvants.

It has now been found that the solutions obtainable in accordance with the invention demonstrate in vitro the same antibacterial activity as would be expected for the combination of the corresponding sulfonamide and the potentiator.

The invention provides a process for the preparation of aqueous solutions of potentiated sulfonamides based on a compound of the formula

$$R^1-CH-(R)_2 \qquad I$$

wherein $R^1$ is hydrogen or an organic group and R is an antibacterially active sulfonamide bonded via the amino group, and a sulfonamide potentiator, and dry residues of such solutions, which process comprises dissolving a compound of formula I, a sulfonamide potentiator and, if desired, a sulfonamide salt corresponding to the compound of formula I or a sulfonamide corresponding to the compound of formula I and an amount of base equivalent to the sulfonamide in water; or dissolving a compound of formula I and a sulfonamide potentiator in an inert, aprotic, organic solvent, thereafter removing the solvent and dissolving the residue in water which contains an amount of base equimolar to the sulfonamide; and, if desired, drying the solution.

The compounds of formula I can be obtained by reacting an antibacterially active sulfonamide in acidic solution with an aldehyde of the formula $R^1$—CHO.

Examples of antibacterially active sulfonamides, bonded in the amino group and present as R are preferably $N^1$-heterocyclic substituted sulfonamides such as those having a 5- or 6-membered heterocycle, for example, a pyrimidine, pyrazine, pyridazine, oxazole or isoxazole ring. Specific examples of sulfonamides are sulfadiazine, sulfamethoxazole, sulfatroxazole, sulfamerazine, sulfadoxine, sulfadimethoxine, sulfamethazine, sulfaquinoxaline, sulfachloropyridazine, sulfaguanidine, sulfalene, sulfametin, sulfamethoxine, sulfamethoxypyridazine, sulfamethylphenazole, sulfaphenazole, sulfamoxole, sulfapyrazine, sulfapyridazine, sulfapyridine, sulfasymazine and sulfametrole.

The expression "potentiator" denotes compounds which increase the antibacterial activity of sulfonamides more than additively. Such sulfonamide potentiators are especially compounds which inhibit dihydrofolate reductase, preferably, 2,4-diaminopyrimidine derivatives. Examples of such 2,4-diaminopyrimidine derivatives are 2,4-diamino-5-benzylpyrimidines which are substituted in the phenyl ring, such as, 2,4-diamino-5-(3,4,5-trimethoxybenzyl)pyrimidine (trimethoprim), 2,4-diamino-5-(3,5-dimethoxy-4-methoxyethoxybenzyl)-pyrimidine (tetroxoprim) and 2,4-diamino-5-(3,5-dimethoxy-4-methylthiobenzyl)-pyrimidine (metioprim). Other examples of dihydrofolate reductase inhibitors are 2,4-diamino-5-(4-bromo-3,5-dimethoxybenzyl)-pyrimidine, 2,4-diamino-5-[3,5-diethoxy-4-(pyrrol-l-yl)-benzyl]-pyrimidine, 2,4-diamino-5-(3,5-dimethoxy-4-dimethylaminobenzyl)-pyrimidine, 2,4-diamino-5-(3,4-dimethoxybenzyl)-pyrimidine (diaveridine), 2,4-diamino-5-(p-chlorophenyl)-6-ethylpyrimidine (pyrimethamine) and 2,4-diamino-5-(2-methyl-4,5-dimethoxybenzyl)-pyrimidine.

The aldehyde of the formula $R^1CHO$ used for the preparation of the compounds of formula I is preferably a lower aliphatic aldehyde, especially formaldehyde. Examples of other aldehydes which can be used are glycol aldehyde and glyceraldehyde. Accordingly, $R^1$ is preferably lower alkyl or most preferably, hydrogen.

The reaction of a sulfonamide with an aldehyde of the formula $R^1CHO$ to prepare a compound of formula I is conveniently carried out by dissolving the sulfonamide in water with the addition of an acid and treating the solution, which is filtered, if desired, with aqueous aldehyde solution, whereby the compound of formula I precipitates and can be isolated, for example, by filtering the solution. A mineral acid acid such as hydrochloric acid is conveniently used as the acid. The acid concentration is not critical within a narrow range; it can be, for example, 0.1–2 normal, preferably, 1 normal. The reaction can be carried out by mixing the reactants, conveniently, at room temperature.

Of particular interest as ingredients in the preparations obtainable in accordance with the invention are combinations of trimethoprim with compounds of formula I which are derived from sulfamethoxazole, sulfadiazine, sulfadoxine and sulfametrole, combinations of tetroxoprim and sulfadiazine compounds of formula I and combinations of pyrimethamine and sulfadoxine compounds of formula I.

The preparation, in accordance with the invention, of the aqueous solutions cn be carried out by mixing the ingredients and heating the mixture conveniently up to about 80° C.

In another embodiment of the invention, a compound of formula I and a potentiator are dissolved in an inert, aprotic, organic solvent, for example, dioxane, preferably while heating for example, up to about 80° C., and the solvent is removed, for example, by evaporation. The thus-obtained solvent-free residue can be dissolved in water with the addition of an amount of base equivalent to the sulfonamide present.

The amount of sulfonamide or of a compound of formula I present in the solutions obtainable in accordance with the invention is governed by the therapeutic activity of the sulfonamide-potentiator combinations. In the commercial combinations the molar ratio sulfonamide:potentiator is $\geq 1:1$, the case of commercial combination of sulfamethoxazole:trimethoprim it is, for exmaple, about 5.7:1, which corresponds to a weight ratio of 5:1. To prepare a solution containing such a combination, there are conveniently used per mol of potentiator $\geq 0.5$ mol, preferably 1.5 to 2.5 mol, of a compound of formula I. If desired, additional amounts of sulfonamide can be added to the solution, the sulfonamide being used in the form of a salt or an amount of base equivalent to the additional sulfonamide being added to the solution. As bases for the salt formation there come into consideration, for example, alkali hydroxides such as sodium or potassium hydroxide, pharmaceutically acceptable organic bases such as N-methylglucamine or basic amino acids such as lysine, arginine or ornithine.

The concentration of the thus-prepared solutions that is the content of dissolved substances, can amount to 40 weight percent or more, 10–20 weight percent solutions preferably being prepared. In the case of certain sulfonamide-potentiator combinations, it is convenient during the preparation to add to the solution a suitable organic solvent which is miscible with water, such as, glycolfurol or polyethylene glycol 400.

The solutions can be dried by means of known galenical techniques, for example, by freeze-drying or spray-drying. The thus-obtained dry preparations, which are also an object of the invention, can, if desired after sterilization, be re-converted into solutions, for example, solutions for injections by the addition of water.

Furthermore, the solutions can be sterilized by means of techniques which are usual in galenics for the preparation of parenteral administration forms, for example, by heat sterilization or sterile filtration.

The applicability of the compounds of formula I in accordance with the invention is not limited to the preparation of injection solutions. The compounds of formula I can also be used for other purposes, that is, when a sulfonamide-potentiator combination in dissolved form should be used.

The preparations made from compounds of formula I and sulfonamide potentiator exhibit in vitro and in vivo the known antibacterial activity of the corresponding sulfonamide-potentiator combinations and can accordingly be used for the same indications.

The Examples which follow further illustrate the invention. The temperatures are given in degrees Centigrade, unless otherwise stated.

EXAMPLE 1

Preparation of $N^4,N^{4'}$-methylene-bis[$N^1$-(5-methyl-3-isoxazolyl)sulfanilamide]

38 g of sulfamethoxazole were almost completely dissolved at 25° in a mixture of 150 ml of concentrated hydrochloric acid and 1350 ml of water while stirring, immediately filtered and treated while stirring with 19.2 ml of about 35% formaldehyde solution. The resulting suspension was stirred for an additional 10 minutes. The solid product was removed by filtration under suction and washed three times with 150 ml of water each time. After drying, there were obtained 27 g of $N^4,N^{4'}$-methylene-bis[$N^1$-(5-methyl-3-isoxazolyl)sulfanilamide] of melting point 180°–188°.

EXAMPLE 2

Preparation of Injectable Formulation 100 mg of trimethoprim were added to a solution of 570 mg of $N^4$, $N^{4'}$-methylene-bis[$N^1$-(5-methyl-3-isoxazolyl)sulfanilamide] and 242 mg of sulfamethoxazole in 3.15 ml of sodium hydroxide and 5 ml of water. The suspension was heated to 80° for 10 minutes. After cooling to room temperature, the total volume was made up to 10 ml with water. This solution can be lyophilized at $-32°$. The lyophilizate can be dissolved in 5 ml of water for injection purposes.

EXAMPLE 3

Preparation of Injectable Formulation

To a solution of 0.8 g of trimethoprim in 150 ml of dioxane were added successively at room temperature a solution of 2.86 g of $N^4,N^{4'}$ -methylene-bis[$N^1$-(5-methyl-3-isoxazolyl)sulfanilamide] in 150 ml of dioxane and 1.22 g of sulfamethoxazole in 150 ml of dioxane. The slightly turbid solution was heated at 85° for 1 hour, cooled to 25°, filtered and the solvent was removed under reduced pressure. The solid residue was dissolved in 15.75 ml of 1N sodium hydroxide and the total volume was made up to 25 ml with water. This solution can be lyophilized at $-32°$. The lyophilizate can be dissolved in 25 ml of water for injection purposes.

I claim:

1. A process for the preparation of an aqueous solution of a potentiated sulfonamide based on a compound of the formula $$R^1-CH-(R)_2 \qquad \text{I}$$

wherein $R^1$ is hydrogen,

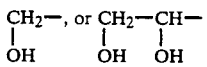

and R is an antibacterially active sulfonamide selected from the group consisting of sulfadiazine, sulfamethoxazole, sulfatroxazole, sulfamerazine, sulfadoxine, sulfadimethoxine, sulfamethazine, sulfaquinoxaline, sulfachloropyridazine, sulfalene, sulfametin, sulfamethoxine, sulfamethoxypridazine, sulfamethylphenazole, sulfaphenazole, sulfamoxole, sulfapyrazine, sulfapyridazine, sulfapyridine, sulfasymazine, and sulfametrole, bonded via the amino group, and a sulfonamide potentiator, which process comprises dissolving a compound of formula I, a sulfonamide potentiator and, a sulfonamide salt corresponding to the compound of formula I or a sulfonamide corresponding to the sulfonamide in the compound of formula I and an amount of base equivalent to the sulfonamide in water.

2. A process for the preparation of a dry residue of an aqueous solution of potentiated sulfonamide based on a compound of the formula

wherein R¹ is hydrogen,

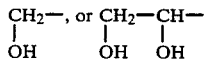

and R is an antibacterially active sulfonamide selected from the group consisting of sulfadiazine, sulfamethoxazole, sulfatroxazole, sulfamerazine, sulfadoxine, sulfadimethoxine, sulfamethazine, sulfaquinoxaline, sulfachloropyridazine, sulfalene, sulfametin, sulfamethoxine, sulfamethoxypyridazine, sulfamethylphenazole, sulfaphenazole, sulfamoxole, sulfapyrazine, sulfapyridazine, sulfapyridine, sulfasymazine, and sulfametrole, bonded via the amino group, and a sulfonamide potentiator, which process comprises dissolving a compound of formula I, a sulfonamide potentiator and, a sulfonamide salt corresponding to the compound of formula I or a sulfonamide corresponding to the sulfonamide in the compound of formula I and an amount of base equivalent to the sulfonamide in water, and, thereafter drying the solution.

3. A process for the preparation of aqueous solution of potentiated sulfonamide based on a compound of the formula

wherein R¹ is hydrogen,

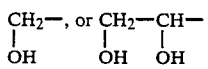

and R is an antibacterially active sulfonamide selected from the group consisting of sulfadiazine, sulfamethoxazole, sulfatroxazole, sulfamerazine, sulfadoxine, sulfadimethoxine, sulfamethazine, sulfaquinoxaline, sulfachloropyridazine, sulfalene, sulfametin, sulfamethoxine, sulfamethoxypyridazine, sulfamethylphenazole, sulfaphenazole, sulfamoxole, sulfapyrazine, sulfapyridazine, sulfapyridine, sulfasymazine, and sulfametrole, bonded via the amino group, and a sulfonamide potentiator, which process comprises dissolving a compound of formula I and a sulfonamide potentiator in an inert, aprotic, organic solvent, removing the solvent and dissolving the residue in water which contains an amount of base equimolar to the sulfonamide.

4. A process for the preparation of a dry residue of an aqueous solution of potentiated sulfonamide based on a compound of the formula

wherein R¹ is hydrogen,

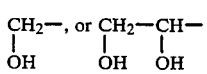

and R is an antibacterially active sulfonanamide selected from the group consisting of sulfadiazine, sulfamethoxazole, sulfatroxazole, sulfamerazine, sulfadoxine, sulfadimethoxine, sulfamethazine, sulfaquinoxaline, sulfachloropyridazine, sulfalene, sulfametin, sulfamethoxine, sulfamethoxypyridazine, sulfamethylphenazole, sulfaphenazole, sulfamoxole, sulfapyrazine, sulfapyridazine, sulfapyridine, sulfasymazine, and sulfametrole, bonded via the amino group, and a sulfonamide potentiator, which process comprises dissolving a compound of formula I and a sulfonamide potentiator in an inert, aprotic, organic solvent, removing the solvent and dissolving the residue in water which contains an amount of base equimolar to the sulfonamide, and, thereafter, drying the solution.

5. A process in accordance with claim 1, wherein the sulfonamide potentiator is selected from the group consisting of 2,4-diamino-5-(3,4,5-trimethoxybenzyl)-pyrimidine, 2,4-diamino-5-(3,5-dimethoxy-4-methoxyethoxybenzyl)-pyrimidine, 2,4-diamino-5-(3,5-dimethoxy-4-methylthiobenzyl)-pyrimidine, 2,4-diamino-5-(4-bromo-3,5-dimethoxybenzyl)-pyrimidine, 2,4-diamino-5-[3,5-diethoxy-4-(pyrrol-1-yl)-benzyl]-pyrimidine, 2,4-diamino-5-(3,5-dimethoxy-4-dimethylaminobenzyl)-pyrimidine, 2,4-diamino-5-(3,4-dimethoxy-benzyl)-pyridimidine, 2,4-diamino-5-(p-chlorophenyl)-6-ethylpyrimidine and 2,4-diamino-5-(2-methyl-4,5-dimethoxy-benzyl)-pyrimidine.

6. A process in accordance with claim 2, wherein the sulfonamide potentiator is selected from the group consisting of 2,4-diamino-5-(3,4,5-trimethoxybenzyl)-pyrimidine, 2,4-diamino-5-(3,5-dimethoxy-4-methoxyethoxybenzyl)-pyrimidine, 2,4-diamino-5-(3,5-dimethoxy-4-methylthiobenzyl)-pyrimidine, 2,4-diamino-5-(4-bromo-3,5-dimethoxybenzyl)-pyrimidine, 2,4-diamino-5-[3,5-diethoxy-4-(pyrrol-1-yl)-benzyl]-pyrimidine, 2,4-diamino-5-(3,5-dimethoxy-4-dimethylaminobenzyl)-pyrimidine, 2,4-diamino-5-(3,4-dimethoxy-benzyl)-pyridimidine, 2,4-diamino-5-(p-chlorophenyl)-6- ethylpyrimidine and 2,4-diamino-5-(2-methyl-4,5-dimethoxy-benzyl)-pyrimidine.

7. A process in accordance with claim 3, wherein the sulfonamide potentiator is selected from the group consisting of 2,4-diamino-5-(3,4,5-trimethoxybenzyl)-pyrimidine, 2,4-diamino-5-(3,5-dimethoxy-4-methoxyethoxybenzyl)-pyrimidine, 2,4-diamino-5-(3,5-dimethoxy-4-methylthiobenzyl)-pyrimidine, 2,4-diamino-5-(4-bromo-3,5-dimethoxybenzyl)-pyrimidine, 2,4-diamino-5-[3,5-diethoxy-4-(pyrrol-1-yl)-benzyl]-pyrimidine, 2,4-diamino-5-(3,5-dimethoxy-4-dimethylaminobenzyl)-pyrimidine, 2,4-diamino-5-(3,4-dimethoxy-benzyl)-pyridimidine, 2,4-diamino-5-(p-chlorophenyl)-6-ethylpyrimidine and 2,4-diamino-5-(2-methyl-4,5-dimethoxy-benzyl)-pyrimidine.

8. A process in accordance with claim 4, wherein the sulfonamide potentiator is selected from the group consisting of 2,4-diamino-5-(3,4,5-trimethoxybenzyl)-pyrimidine, 2,4-diamino-5-(3,5-dimethoxy-4-methoxyethoxybenzyl)-pyrimidine, 2,4-diamino-5-(3,5-dimethoxy-4-methylthiobenzyl)-pyrimidine, 2,4-diamino-5-(4-bromo-3,5-dimethoxybenzyl)-pyrimidine, 2,4-diamino-5-[3,5-diethoxy-4-(pyrrol-1-yl)-benzyl]-pyrimidine, 2,4-diamino-5-(3,5-dimethoxy-4-dimethylaminobenzyl)-pyrimidine, 2,4-diamino-5-(3,4-dimethoxy-benzyl)-pyridimidine, 2,4-diamino-5-(p-chlorophenyl)-6-ethylpyrimidine and 2,4-diamino-5-(2-methyl-4,5-dimethoxy-benzyl)-pyrimidine.

9. A process in accordance with claim 5, 6, 7 or 8 wherein in the compound of formula I $R^1$ is hydrogen.

10. A process in accordance with claim 5, 6, 7 or 8 wherein in the compound of formula I R is the residue of sulfamethoxazole, sulfadiazine, sulfadioxine or sulfametrole bonded via the amino group, and $R^1$ is hydrogen.

11. A process in accordance with claim 5, 6, 7 or 8 wherein in the compound of formula I R is the residue of sulfamethoxazole bonded via the amino group.

12. A process in accordance with claim 11, wherein the potentiator is trimethoprim.

* * * * *